United States Patent
Nalepa et al.

[11] Patent Number: 5,968,459
[45] Date of Patent: Oct. 19, 1999

[54] FILTERED FLASH STERILIZATION APPARATUS

[75] Inventors: David Nalepa, Manasquan; Allan S. Frieze; Marcia A. Frieze, both of Alpine, all of N.J.

[73] Assignee: Case Medical, Inc., Ridgefield, N.J.

[21] Appl. No.: 09/023,055

[22] Filed: Feb. 12, 1998

[51] Int. Cl.⁶ .................................................. A61L 2/00
[52] U.S. Cl. .................... 422/300; 422/292; 422/297; 206/439; 215/308; 220/315; 220/371; 220/913
[58] Field of Search ............................... 422/26, 27, 292, 422/297, 300; 206/439; 220/371, 315, 324, 327, 254, 293, 297, 913; 215/308

[56] References Cited

U.S. PATENT DOCUMENTS

| | | | |
|---|---|---|---|
| 4,617,178 | 10/1986 | Nichols | 422/300 |
| 4,716,025 | 12/1987 | Nichols | 422/300 |
| 4,728,504 | 3/1988 | Nichols | 422/300 |
| 4,783,321 | 11/1988 | Spence | 422/300 |
| 5,098,676 | 3/1992 | Brooks | 422/292 |
| 5,324,489 | 6/1994 | Nichols et al. | 422/300 |
| 5,372,787 | 12/1994 | Ritter | 422/300 |
| 5,474,738 | 12/1995 | Nichols et al. | 422/300 |
| 5,524,755 | 6/1996 | Deeds | 206/439 |
| 5,628,970 | 5/1997 | Basile et al. | 422/300 |
| 5,732,821 | 3/1998 | Stone et al. | 206/439 |

FOREIGN PATENT DOCUMENTS

| | | | |
|---|---|---|---|
| 202334 | 7/1956 | Australia | 220/297 |

*Primary Examiner*—Elizabeth McKane
*Assistant Examiner*—Fariborz Moazzam
*Attorney, Agent, or Firm*—Woodbridge & Associates

[57] ABSTRACT

A flash sterilization container (10) comprises a pan (12) forming the bottom of the container holding a tray (14), with a cover (16) forming the top of the container, and a filter element (20). The filter (20) covers an opening in the cover (16) so that the inside of the container (10) formed when the cover is removably sealed to the pan (12) can communicate with the atmosphere surrounding the sealed container allowing steam to enter and exit the container passing through the filter (20). Items to be sterilized are placed on the tray (14) and the cover (16) is attached and sealed to the pan (12). The sealed container in then placed in an autoclave or other source of pressurized steam. The filter (20) allows the steam to enter the interior of the container and sterilize any items contained therein. After sterilization, the container (10) is removed from the autoclave and any remaining steam escapes from the interior of the container through the filter (20). The filter is composed of a material which will allow the pressurized steam to pass through but which is relatively impervious to dust and microorganisms thereby maintaining the sterility of the interior of the container and it's contents. Examples of suitable filter materials are: paper; TEFLON®; hydrophobic material, such as GORE-TEX®; porous stainless steel and polysulfone. The filter (20) can be held in place with a filter retainer manufactured as a permanent part of the cover (16) or incorporated into a filter cartridge which is removably attached to the cover.

8 Claims, 7 Drawing Sheets

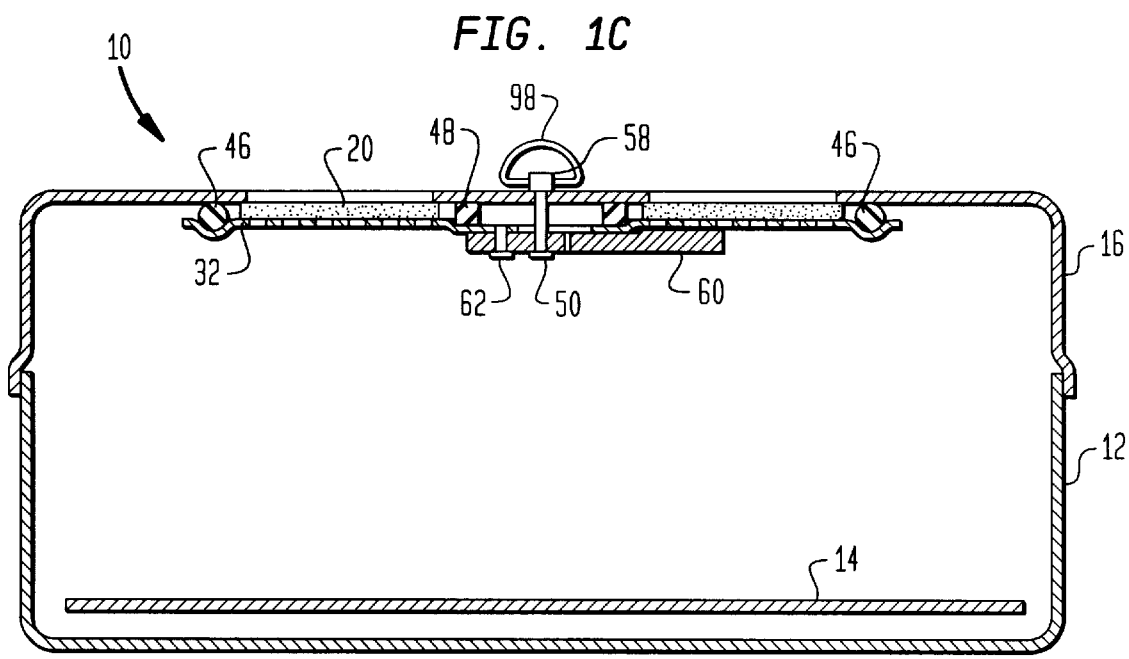

FILTERED FLASH STERILIZATION APPARATUS

BACKGROUND OF THE INVENTION

1. Field of the Invention

The invention relates, in general, to a method for sterilizing medical instruments with steam and, in particular, to a sterilization container useful for flash sterilization which includes a filter that permits maximum steam penetration and prevents microorganisms and dust from entering.

2. Description of Related Art

Steam sterilization is a common method used for the sterilization of items, especially medical instruments by processing the items in an autoclave and exposing them to high pressure steam. This method requires the wrapping of individual items, heating the items with steam and then waiting for a drying/cooling period. Often during surgical procedures commonly used instruments need to be quickly sterilized after use or inadvertent contamination. Under such circumstances the standard autoclave method would take too long. An alternative sterilization method, which can be used under these circumstances, is known as flash sterilization. In flash sterilization metal instruments are not wrapped and are heated directly by the steam allowing sterilization in a reduced period of time. One drawback to the use of flash sterilization is the lack of a drying period. When the items are still moist and hot from sterilization, microorganisms and dust can contaminate the items when they are transported from the autoclave/sterilizer.

One common design for containers for flash sterilization is described in U.S. Pat. Nos. 5,097,865 and 4,748,003. Such containers use valves which require greater than atmospheric pressures to open the valves and allow the high pressure steam to enter the container but are closed under normal pressure conditions. This approach has a number of disadvantages. Such containers must be opened to allow the steam to escape, thus breaking the sterile field. Even if kept sealed, these containers cannot maintain the sterile field for longer than 24 hours. Also, the high temperature, high pressure valves needed for this method are very complex and very expensive.

The present invention facilitates the use of flash sterilization while retaining the advantage of standard autoclave sterilization by maintaining the sterility of the items in the sterilization container. Instead of a costly, complicated valve system the present invention uses a passive filter system which is capable of allowing steam to enter and exit the container and still keeping microorganisms and dust out, maintaining the sterile field in the container for long term storage.

SUMMARY OF THE INVENTION

Briefly described, the invention comprises a sterilization container and a flash sterilization method for sterilizing items, which allow for extended, sterile storage of the sterilized items. The flash sterilization method uses a sterilization container having a pan, a cover and one or more filters for preventing dust and microorganisms from entering the container and contaminating the sterilized items while still allowing steam in and out of the container during the sterilization process. These containers can be used in the flash sterilization process commonly used in surgical theaters. The filter can be permanently mounted in the container or can be removable for replacement with new or different types of filters. Removable filters will allow for the retrofitting of currently used containers with the filters so that new containers do not need to be purchased to take advantage of the filtered flash sterilization method of the present invention. The filter can be removably attached to the container, manufactured as an integral part of the container, or incorporated into a self-contained removable filter unit.

Another aspect of the present invention comprises a novel filter retainer used for attaching a filter to the sterilization container. The filter retainer has a plurality of steam penetration holes which can be of various sizes and shapes allowing sufficient steam to enter the container. The filter retainer also comprises one or more gaskets for maintaining a seal between the filter retainer and the sterilization container as well as a locking means for removably attaching the retainer to the container.

These and other features of the invention may be more fully understood by reference to the following drawings.

BRIEF DESCRIPTION OF THE DRAWINGS

FIG. 1C is a perspective view of the flash sterilization container invention with the top surface of the lid having a D-ring attached to it.

DETAILED DESCRIPTION OF THE INVENTION

During the course of this description like numbers will be used to identify like elements accordingly to the different figures that illustrate the invention.

Figure 1A:
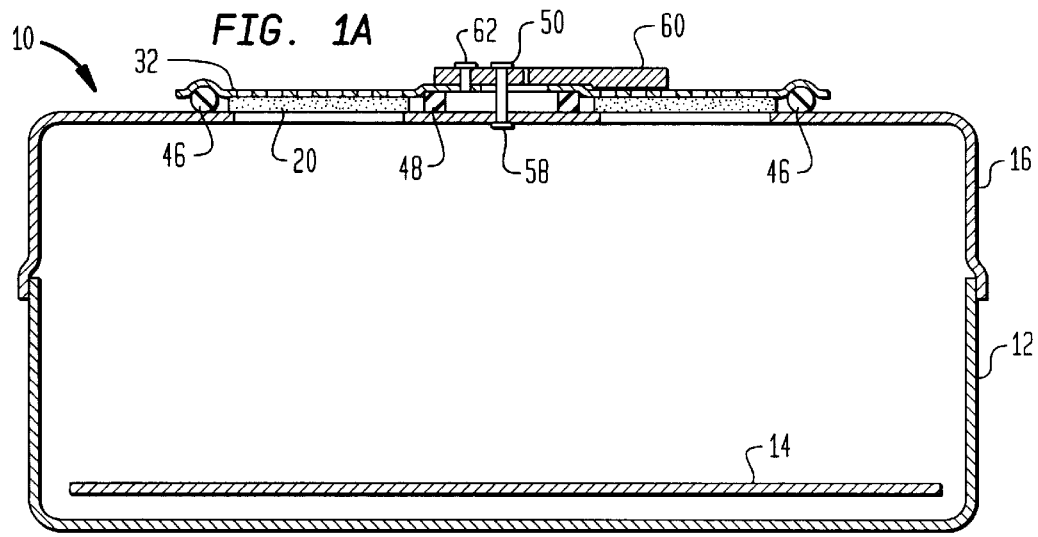
FIG. 1A is a perspective view of the preferred embodiment of the flash sterilization container invention.
Figure 1B:
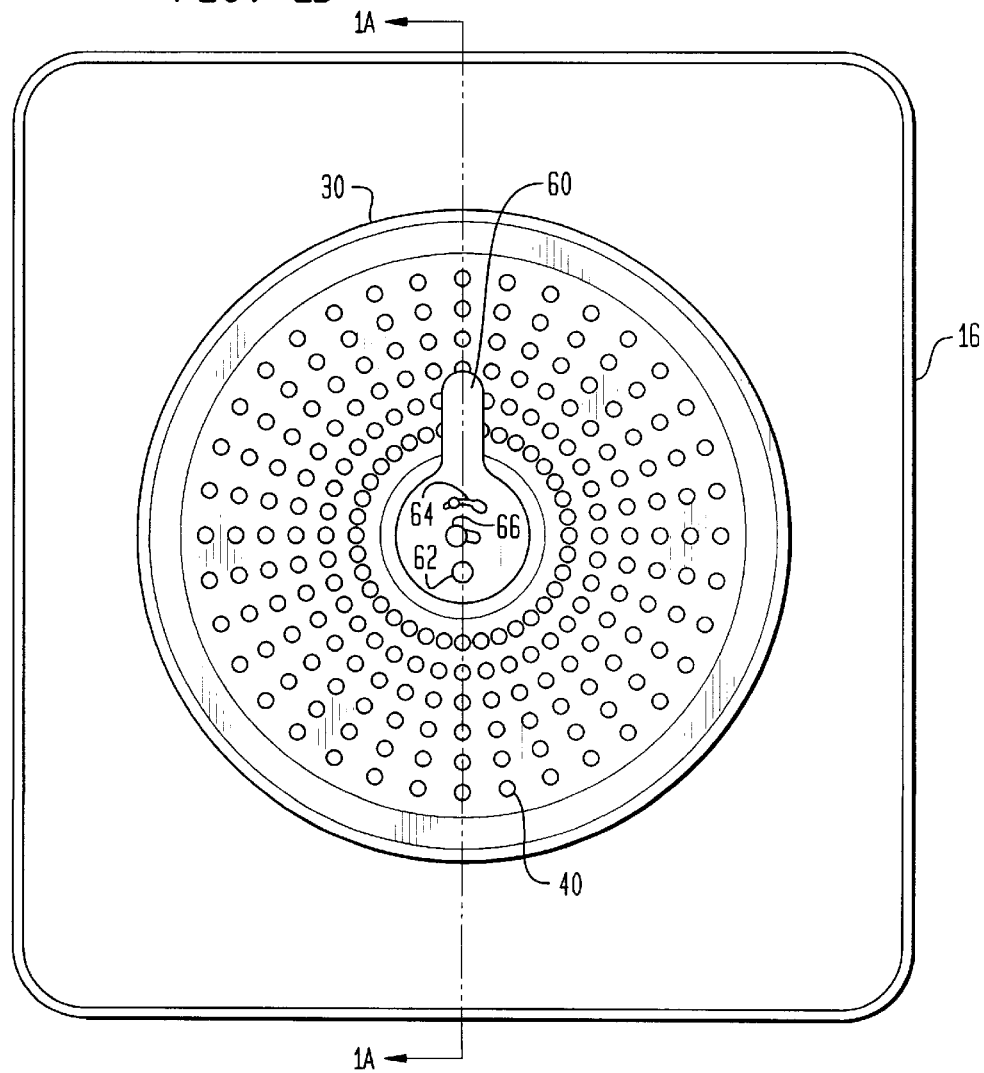
FIG. 1B is a top perspective view of the flash sterilization container cover with a filter retainer.

The flash sterilization container invention 10 according to a preferred embodiment thereof is illustrated in FIG. 1. A sterilization container 10 comprises a pan 12 which forms the bottom of the container which holds and supports a conventional sterilizable tray 14, and a cover 16 which forms the top of the container. The cover is removably attached to the pan to form a hermetically sealed container. This can be accomplished by conventional means such as hinges and clamps and a sealing gasket. The cover 16 is provided with an opening 18 at its top. This opening 18 is covered with a filter 20 to allow steam to enter and exit the container through the opening by passing through the filter. The filter can be removably or permanently attached to the cover. This filter is made of a material, or combination of materials, such that the filter is permeable to the flow of steam but will inhibit dust or other airborne particles or microorganisms from passing through. Examples of such materials include paper, TEFLON®, porous stainless steel, polysulfone, and hydrophobic material, such as GORE- TEX®. TEFLON® is a registered trademark of the E.I. du Pont de Nemours and Company, Inc., Wilmington, Del. and GORE-TEX® is a registered trademark of the W.L. Gore & Associates, Inc., Newark, Del. The filter is attached to the cover by means which will prevent any steam, dust or other airborne particles or microorganism to pass through the opening in the cover without passing through the filter.

In the preferred embodiment, the filter 20 is placed over the opening 18 in the top of the cover 16 and the filter is attached to the cover by a filter retainer 30. The preferred embodiment of such a filter retainer is illustrated in FIGS. 1A, 1B, 2A, 3A and 3B. Filter retainer 30 comprises a filter retainer disc 32 and a means for sealing the filter retainer disc to the cover. The filter retainer disc has an inner disc 34, a middle ring 36, and an outer ring 38. Middle ring 36 has a plurality of holes 40 to allow the flow of steam through the filter retainer disc 32, through the filter 20, and through the opening 18 in the cover 16. The filter retainer can have one or more sealing means for forming a seal between the filter and the cover. The outer ring 38 has a means for forming a seal between the filter and the cover. In one embodiment the outer ring has an inverted-u shaped cross-section. A gasket 46 is placed in the inverted-U outer ring and can be made of silicone, neoprene, TEFLON® or any other suitable material. Inner disc 34 may also have a sealing means if necessary, such as a gasket 48.

Figure 2A:
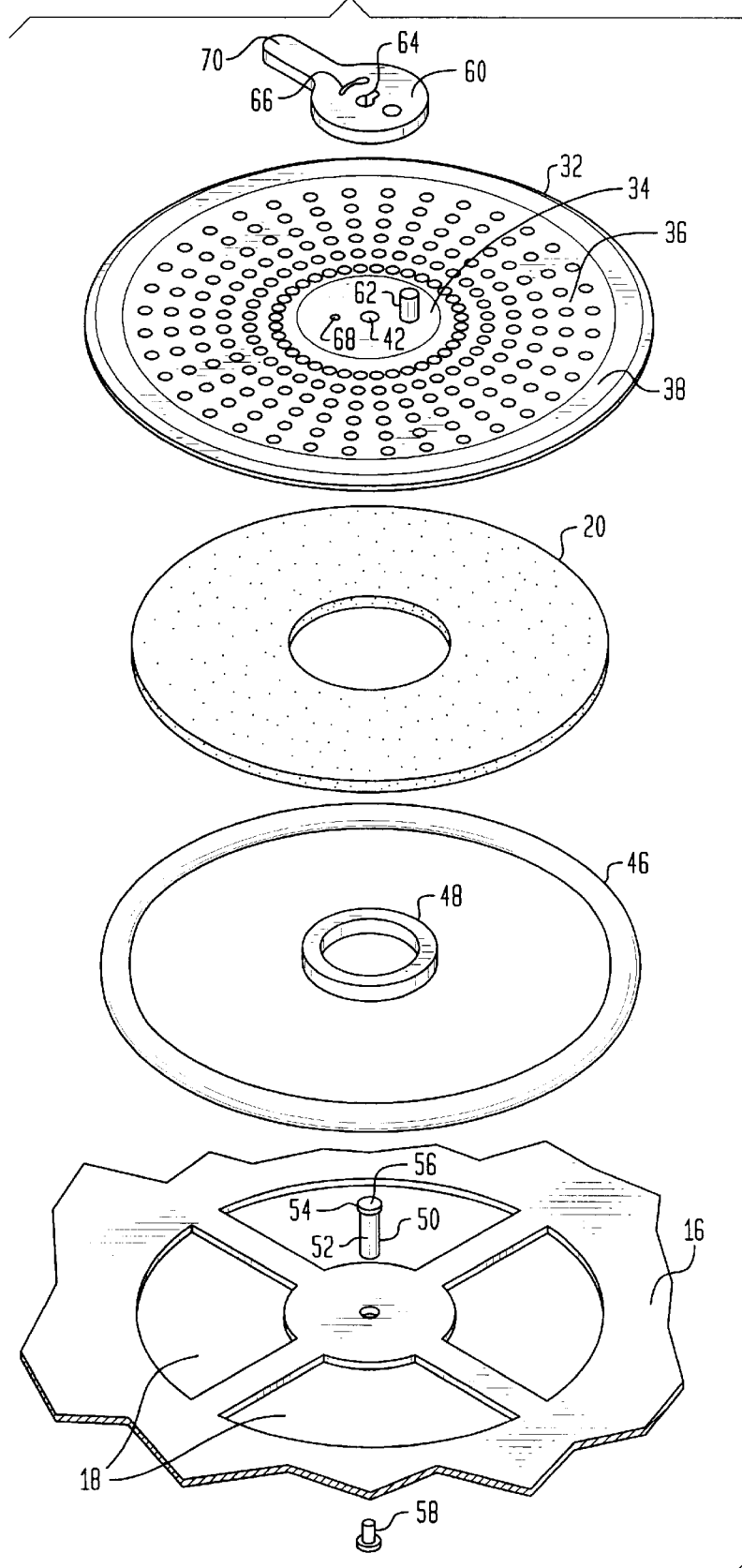
FIG. 2A is an exploded perspective view of the flash sterilization container filter invention.
Figure 2B:
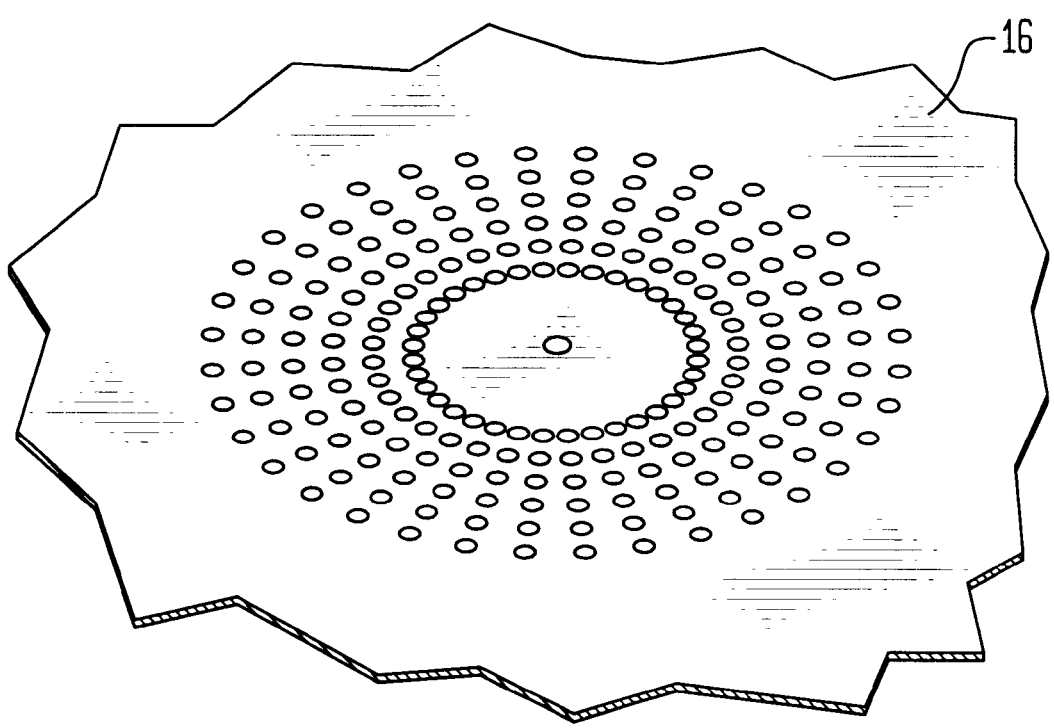
FIG. 2B is a partial view of a cover opening configuration.
Figure 3A:
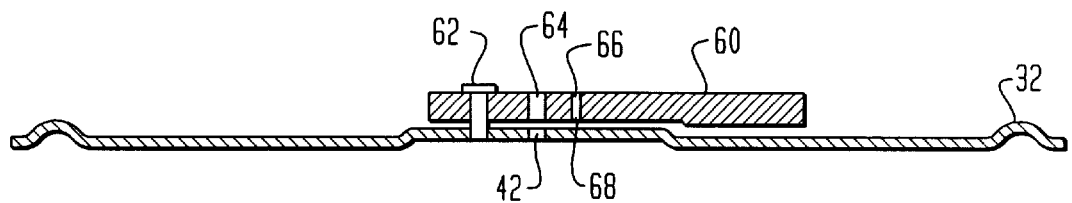
FIG. 3A is a side elevational view of the filter retainer invention.
Figure 3B:
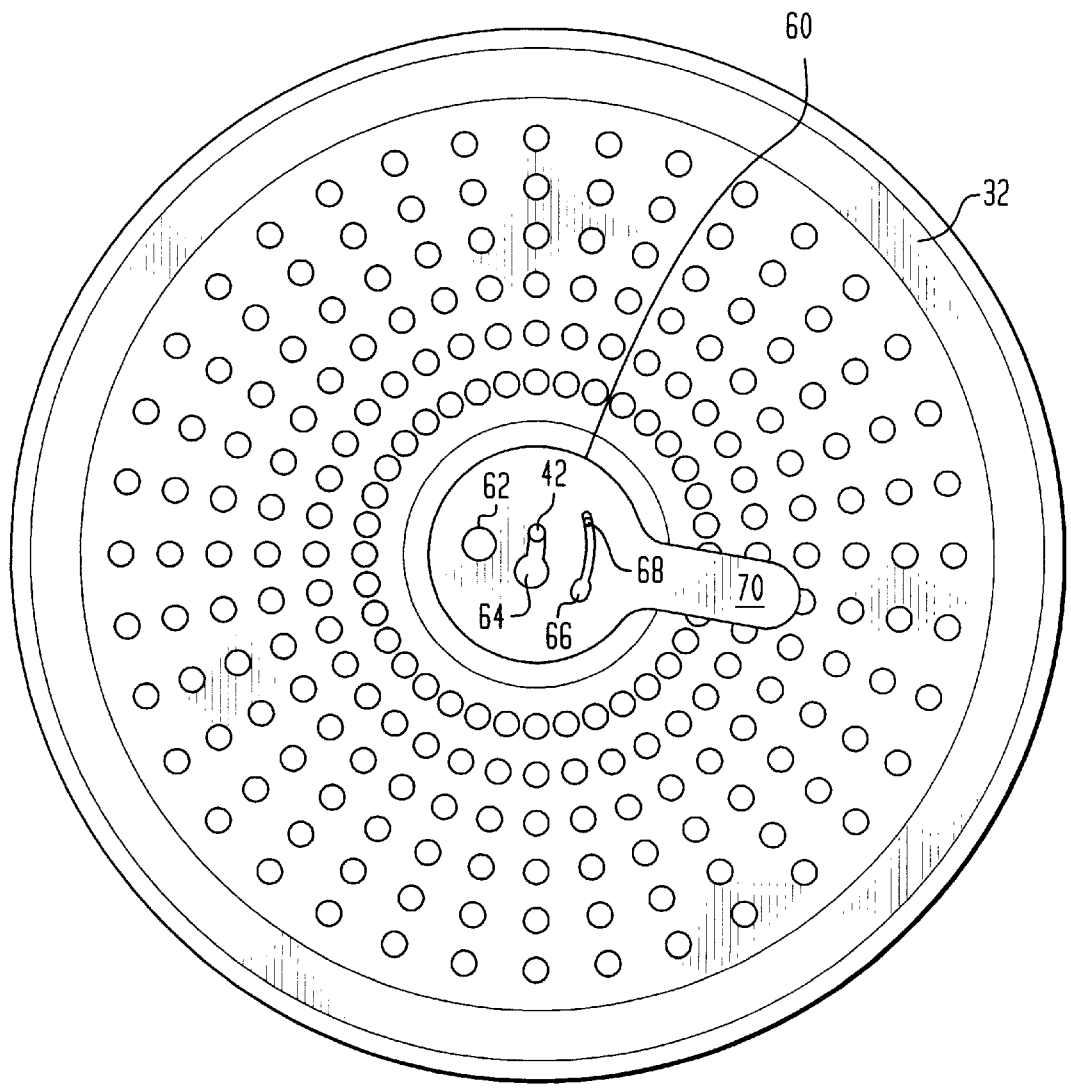
FIG. 3B is a top plan view of the filter retainer invention with the locking means in the locked position.
Figure 3C:
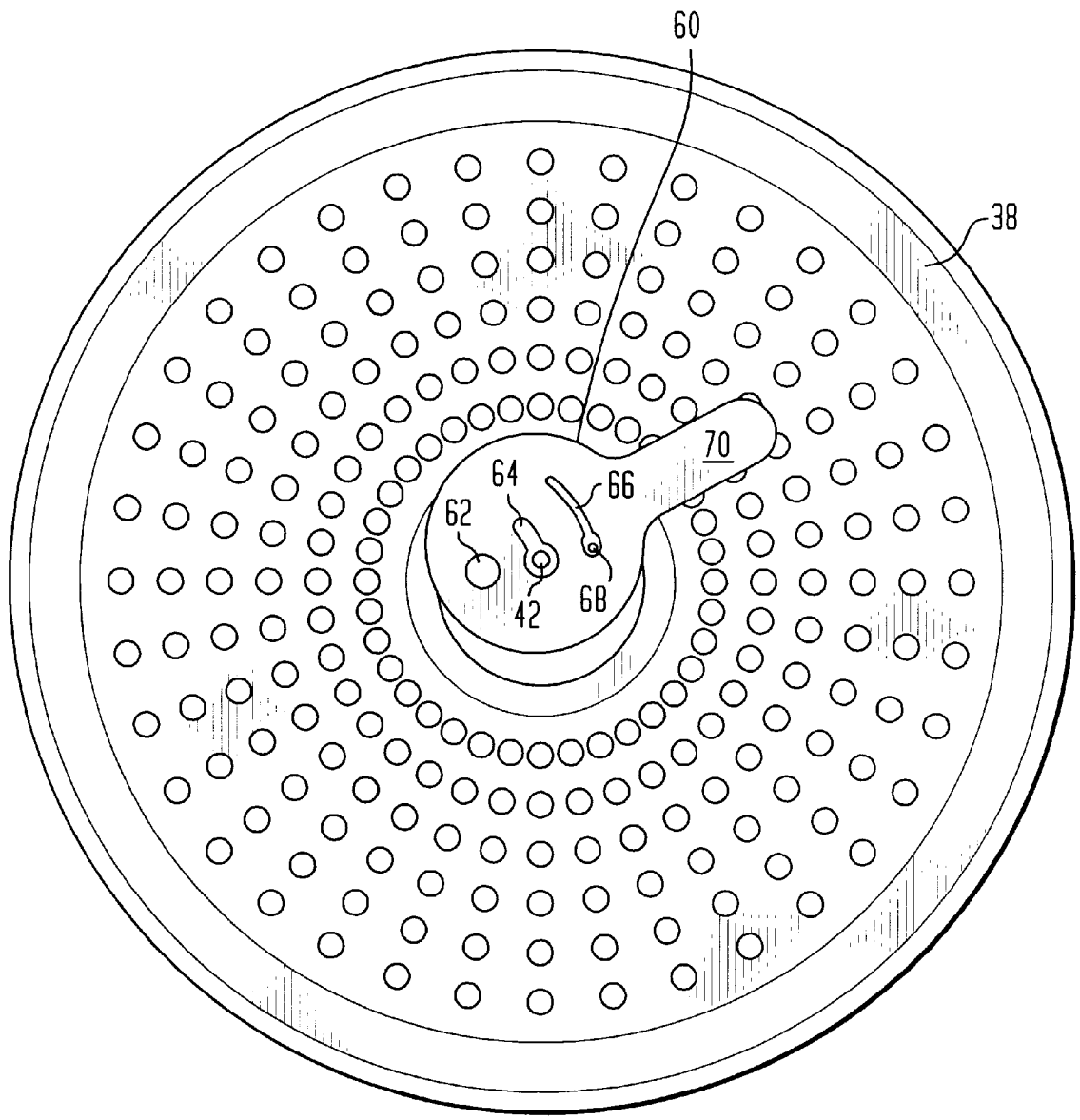
FIG. 3C is a top plan view of the filter retainer invention with the locking means in the unlocked position.

The preferred embodiment of a means for attaching the filter retainer to the cover is illustrated in FIGS. 1A, 1B, 2A, 3A, and 3B. Pin 50 extends upwards from the top surface of the cover 16. Inner disc 34 of the filter retainer disc 32 has a hole 42 for accepting pin 50. Pin 50 has sufficient length to extend past the top surface of the filter retainer 30 when the filter retainer is placed on the cover 16 allowing the hole in the inner disc 42 to engage the pin 50. Pin 50 is preferably located in the center of the opening 18 in the cover 16. To locate the pin in the proper position, the opening in the cover can be, for example, a circular opening with cross pieces such as those illustrated in FIG. 2A. In an alternate embodiment, the opening in the cover can be comprised of a multiplicity of smaller openings in the cover, as depicted in FIG. 2B. A locking means is located on the inner disc which engages the pin 50 and holds the filter retainer in place.

The preferred locking means is comprised of a sliding plate 60 which is movably attached to the inner disc 34 of the filter retainer disc 32 with a hinge pin 62 extending from the inner disc 34 of the filter retainer disc 32, so that the sliding plate 60 rotates about the center of the hinge pin 62 while remaining in contact with the inner disc. The sliding plate 60 has an arc-shaped pin slot 64 having an effective radius equal to the distance from the hinge pin 62 to the hole in the center of the inner disc 42, whereby the center of the hole in the inner disc maintains alignment with the center of the arc-shaped slot throughout the rotation of the sliding plate.

The retainer pin 50 is comprised of a cylindrical body 52 having opposite ends and an outside diameter essentially equal to the inside diameter of the hole 42 in the filter retainer disc, a cylindrical neck 54 having a diameter smaller than the diameter of the body and equal to the width of the arc shaped slot 64, and a cylindrical head 56 having a top and a bottom and having a diameter larger than the pin neck 54, preferably equal to the diameter of the pin body 52. One end of the pin body 52 is attached to the cover 16 by conventional means, such as, a rivet 58, a screw, a thread, or a spot weld. Pin neck 54 is attached to the end of the pin body 52 opposite the attachment to the cover. The bottom of the pin head is attached to the pin neck at the end opposite the pin neck's attachment to the pin body. The retainer pin can be made of separate elements attached by conventional means or preferably manufactured from a single piece of stock. The length of the pin body is essentially equal to the distance from the top surface of the cover to the top surface of the inner disc. The length of the pin neck is at least equal to the thickness of the sliding plate. The combined length of the pin body and pin neck is such that the bottom of the pin head is slightly lower than the top surface of the sliding plate 60 so that when the arc-shaped pin slot 64 engages the pin neck 54, the filter retainer disc 32 will be forced toward the cover, compressing the gaskets 46, 48, and creating a seal between the filter retainer 30 and the cover 16. The top of the pin head 56 can have a taper to facilitate the insertion of the retainer pin 50 through the hole in the filter retainer disc 42 and arc-shaped slot in the sliding plate 64.

The arc shaped slot 64 has a width essentially equal to the outside diameter of the pin neck and a length at least twice as long as the outside diameter of the pin head. At one end of the arc-shaped slot 64, the width of the slot is increased to allow the pin head to pass through the arc-shaped slot.

A filter is attached to the cover with the filter retainer by placing a filter 20 over the hole 18 in the cover 16, the sliding plate 60 is positioned so that the end of the arc-shaped slot 64 having an increased width is aligned with the hole in the inner disc 42, the filter retainer 30 is then placed over the opening in the cover 16 so that the retainer pin 50 passes through the hole in the inner disc 42 and the enlarged end of the arc-shaped slot 64, and the sliding plate 60 is then rotated so that the arc-shaped slot 64 engages the pin neck 54, thereby preventing the pin from passing back through the arc-shaped slot and thus attaching the filter retainer to the cover.

In a preferred embodiment, the filter retainer 30 has a means for limiting the rotation of the sliding plate 60 and facilitating positioning the sliding plate in an "open" position, where the enlarged end of the arc-shaped slot 64 lines up with the hole in the inner disc 42, and a "locked" position, where the opposite end of the arc-shaped slot lines up with the hole in the inner disc. One embodiment of a limiting means incorporates an arc-shaped limiting slot 66 on the sliding plate 60. This arc of the limiting slot 66 is parallel to the arc of the arc-shaped slot 64 and has an effective radius larger than the radius of the arc-shaped slot 64. A locating pin 68 is attached to, and extends from, the inner disc 34 such that it engages one end of the limiting slot 66 when the sliding plate 60 is in the locked position and engages the opposite end of the arc-shaped slot when the sliding plate is in the unlocked position. The locating pin 68 is preferably hemispherical-shaped to facilitate the movement of the sliding plate 60 over the locating pin 68. A hemispherical locating pin 68 can be made, for example, by inserting and attaching a ball bearing in a hole in the inner disc 34. The width of the limiting slot 66 is slightly less than the diameter of the locating pin 68. The width of the limiting slot 66 at each of the two, opposite ends, is enlarged slightly, forming two holes each having a diameter slightly larger than the diameter of the locating pin 68. Consequently, the sliding plate 60 is held in the locked and open positions when the locating pin 68 engages each of the holes in the ends of the limiting slot 66, requiring the application of an external force to move the sliding plate between the two positions.

The sliding plate 60 preferably has a handle 70 to facilitate moving the plate between the open and closed positions. The handle 70 preferably extends parallel to the plane of the sliding plate. The handle 70 can be attached to the sliding plate or manufactured with the sliding plate as a single piece.

Figure 4A:
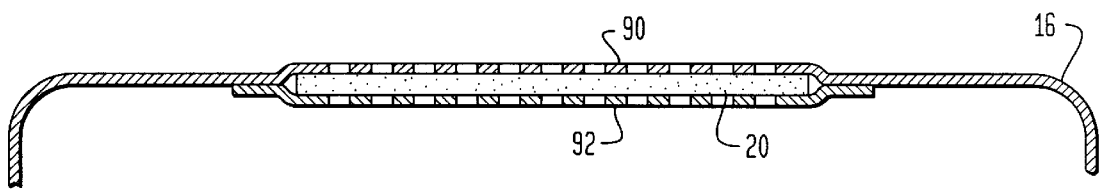
FIG. 4A is a partial, side elevational view of a flash sterilization container cover with an incorporated filter.
Figure 4B:
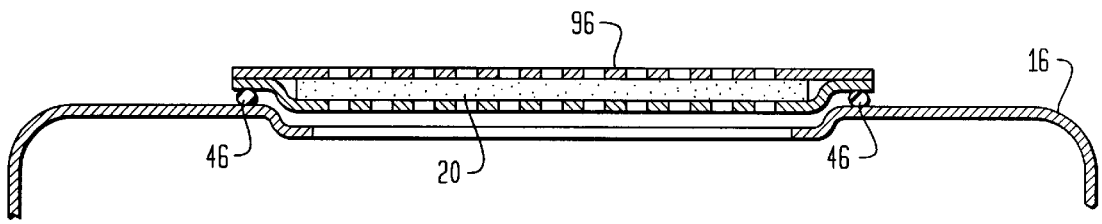
FIG. 4B is a partial, side elevational view of a flash sterilization container and a filter cartridge.

As described above, the preferred embodiment comprises a sterilization container having a filter retainer mechanism. "Alternative embodiments comprise having the filter 20 manufactured as an integral part of the container as depicted in FIG. 4A, in which the filter 20 is sandwiched between two perforated plates 90 and 92 welded together, or having the filter 20 incorporated into a self-contained removable filter unit or cartridge 96 as depicted in FIG. 4B.

A further alternative embodiment comprises a D-ring 98 attached to the end of pin 50 connected to the cover 16. In this embodiment, the filter and filter retainer are mounted on the inside of the sterilization container. This arrangement permits the external D-ring 98 to be used as a handle to lift the cover without coming into contact with the side edges of the cover 16, thereby reducing the risk of contamination of the container contents.

While the invention has been described with reference to the preferred embodiment thereof, it will be appreciated by those of ordinary skill in the art that modifications can be make to the structure and form of the invention without departing from the spirit and scope thereof.

What is claimed is:

1. A sterilization container apparatus (10) used for sterilizing items placed therein, said apparatus (10) comprising:
    a pan (12) for containing a tray (14) and a cover (16) having an opening (18) which is covered by a steam permeable filter (20);
    a cover pin (50) having a first end attached to said cover (16) and a second free end having a head portion (56) attached thereto;
    a filter retainer disc (32) for selectively retaining said filter (20), said filter retainer disc (32) having an aperture means (42) therein which selectively permits said cover pin (50) to pass therethrough;
    a first pin (62) attached to said filter retainer disc (32); and,
    a rotatable locking plate (60) having a first aperture therein for accepting said first pin (62) so that said locking plate (60) can rotate about said first pin (62), said rotatable locking plate (60) also including a second aperture (64) in the form of an arc, said second aperture (64) having a first end and a second end and wherein said second end of said second aperture (64) is wider than said first end,
    wherein said rotatable locking plate (60) selectively locks said filter (20) and said filter retainer disc (32) securely to said cover (16) when said rotatable locking plate (60) is in a first position corresponding to when said cover pin (50) is located at the first end of said second aperture (64) and selectively unlocks a said filter (20) and filter retainer disc (32) from said cover (16) when said rotatable locking plate (60) is rotated to a second position corresponding to when said cover pin (52) is located at said second wider end of said second aperture (64).

2. The apparatus (10) of claim 1 further comprising:
    a third aperture (66) in said rotatable plate (60), said third aperture (66) being in the form of an arc; and,
    a second pin (68) also attached to said filter retainer disc (32),
    wherein said second pin (68) rides in said third aperture (66) and assists in locating said cover pin (52) in said second wider end of said second arc shaped aperture (64).

3. The apparatus of claim 2 further comprising:
    a handle (70) attached to said rotatable locking plate (60).

4. The apparatus (10) of claim 3 further comprising:
    circular gasket means (46) located between said filter retainer disc (32) and said cover (16).

5. The apparatus (10) of claim 4 wherein said filter retainer disc (32) comprises:
    an inner annular disc section (34);
    a middle ring section (36) having vent apertures therein; and,
    an outer ring section (38) including a groove therein for receiving said circular gasket means (46).

6. The Apparatus (10) of claim 5 wherein said filter (20) is impervious to dust particles and microorganisms and comprises a material selected from a group consisting of paper, hydrophobic material, polytetraflouroethylene, porous stainless steel and polysulfone.

7. The apparatus (10) of claim 6 wherein said cover (16) has an inside facing said tray (14) and an outside, and wherein said filter (20), filter retainer disc (32), and said rotatable locking plate (60) are all located on the outside of said cover (16).

8. The Apparatus (10) of claim 6 wherein said cover (16) has an inside facing said tray (14) and an outside, and wherein said filter (20), filter retainer disc (32), and said rotatable locking plate (60) are all located on the inside of said cover (16), and wherein said apparatus (10) further comprises:
    a ring (98) located on the outside of said cover (16) and attached to said first end of said cover pin (52),
    wherein said ring (98) can be used to manually remove said cover (16) from said pan (12).

* * * * *